United States Patent [19]
Yoo et al.

[11] Patent Number: 6,043,373
[45] Date of Patent: Mar. 28, 2000

[54] HETEROCYCLE-FUSED THIAZOLE DERIVATIVES

[75] Inventors: Han Yong Yoo; Kae Jong Chung, both of Seoul; Jun Pyo Chai, Suwon; Man Sik Chang, Seoul; Sung Gyu Kim, Taejeon; Wahn Soo Choi, Seoul; Young Hun Kim, Pyungtack; Jae Kwang Chun, Seoul; Young Kuk Chung, Suwon; Young Heui Kim, Pyungtack; Jang Hoon Paek, Seoul; Kwi Hyon Seo, Suwon; Dae Pil Kang, Pyungtack, all of Rep. of Korea

[73] Assignee: Yungjin Pharmaceutical Co., Ltd., Seoul, Rep. of Korea

[21] Appl. No.: 08/849,739

[22] PCT Filed: Jun. 1, 1996

[86] PCT No.: PCT/KR96/00082

§ 371 Date: Jul. 3, 1997

§ 102(e) Date: Jul. 3, 1997

[87] PCT Pub. No.: WO97/03076

PCT Pub. Date: Jan. 30, 1997

[30] Foreign Application Priority Data

Jul. 12, 1995 [KR] Rep. of Korea ................ 95-20516

[51] Int. Cl.$^7$ .................................................. C07D 513/04
[52] U.S. Cl. ..................... 548/148; 544/368; 546/64; 546/271; 548/149; 548/151
[58] Field of Search .................. 548/148, 149, 548/151; 546/64, 271; 544/368

[56] References Cited

U.S. PATENT DOCUMENTS 4,283,408   8/1981   Hirata et al. ........................... 424/270

FOREIGN PATENT DOCUMENTS 56-5538A    1/1981  Japan.
57-134417A  8/1982  Japan.
91-7976A    5/1991  Rep. of Korea.

OTHER PUBLICATIONS

Babu C.A. vol. 111(1) 7296v 1989.
Smolka et al., "Monoclonal antibodies against gastric H$^+$+K$^+$ ATPase", American Physiological Society, 1983, 245, G589–G596.
Sachs et al., "A Nonelectrogenic H$^+$ Pump in Plasma Membranes of Hog Stomach", The Journal of Biological Chemistry, 1976, 251, 7690–7698.
Fiske et al., "The Colorimetric Determination of Phosphorus", The Journal of Biological Chemistry, 1925, 66, 375–440.
Brezin et al., "Survival Following Massive Resection of Small and Large Bowel; Water, Electrolyte and Blood Volume Studies", Gastroenterology, 1954, 26, 895–905.
Saccomani et al., Biochimica et Biophysica Acta, 1977, 465, 311–330.
Remers et al., J. Heterocycl. Chem., 1975, 12(2), 421–422.

*Primary Examiner*—Robert Gerstl
*Attorney, Agent, or Firm*—Foley & Lardner

[57] ABSTRACT

A thiazole compound represented by general formula (I), wherein R is hydrogen atom, a hydroxy group, a straight or branched $C_1$–$C_6$ lower alkyl group, a $C_1$–$C_4$ lower alkoxy group, phenyl group, a phenyl group having one to three substituents selected from a group consisting of a $C_1$–$C_4$ lower alkyl group, a $C_1$–$C_4$ lower alkoxy group, fluorine, chlorine, bromine and an amino group, a $C_1$–$C_5$ alkylphenyl group, a phenyl group having one to three substituents selected from a group consisting of a $C_1$–$C_4$ lower alkyl group, a $C_1$–$C_4$ lower alkoxy group, fluorine, chlorine, bromine and an amino group, a substituted or unsubstituted guanidino group, or an amino group having a general formula: $NR_3R_4$ in which $R_3$ and $R_4$, identical to or different from each other, represent independently a hydrogen atom, a $C_1$–$C_6$ lower alkyl group, a $C_3$–$C_6$ cycloalkyl group, a substituted or unsubstituted pyridyl group, a phenyl group having one to three substituents selected from a group consisting of a $C_1$–$C_4$ lower alkyl group, a $C_1$–$C_4$ lower alkoxy group, a halogen atom, an amino group, a cyano group and a nitro group, a piperidine group or $C_1$–$C_4$ alkylpiperidine group; $R_1$ and $R_2$, identical to or different from each other, are independently a hydrogen atom, a hydroxy group, a $C_1$–$C_6$ lower alkyl group, phenyl group, a phenyl group having one substituent selected from a group consisting of a $C_1$–$C_4$ lower alkyl group, a $C_1$–$C_4$ lower alkoxy group, a halogen atom, a nitro and a cyano group, a $C_1$–$C_5$ alkylphenyl group, or a pyridine group; $R_5$, $R_6$, $R_7$ and $R_8$, identical to or different from each other, are independently a hydrogen atom, a hydroxy group, a $C_1$–$C_4$ lower alkyl group, a $C_1$–$C_4$ lower alkoxy group, phenyl group, or a phenyl group substituted with a $C_1$–$C_4$ alkyl group, a $C_1$–$C_4$ alkoxy group or a halogen atom, or a $C_1$–$C_3$ alkylphenyl group; Het is a 3-, 4- or 5-membered unsaturated monocyclic group, or 6- to 12-membered unsaturated fused cyclic group, said monocyclic and fused cyclic group being comprised of one or more hetero atoms selected from oxygen, oxidative nitrogen and oxidative sulfur atom are disclosed. These compounds show excellent anti-ulcer activity.

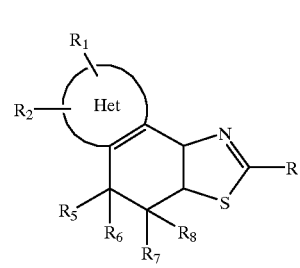

(I)

3 Claims, No Drawings

HETEROCYCLE-FUSED THIAZOLE DERIVATIVES

FIELD OF THE INVENTION

The present invention is related to new thiazole derivatives or their pharmaceutically acceptable salts useful as anti-ulcer agents, and to a method for producing them.

BACKGROUND OF THE INVENTION

It has been reported that the gastrointestinal ulcers may be caused by a excessive secretion of acids such as hydrochloride acid or pepsin as well as by an action of anti-inflammatory agents such as indomethacin, toxic chemicals, pathogenic virus or toxic microorganisms. In particular, it had been reported that $H^+/K^+$ ATPase, an enzyme which plays an important role during the last step of the acid secretion in stomach cell affects the gastric acidity (Am. J. Physiol., 1983, 245, G589, J. Biol. Chem., 1976, 251, 7690). Therefore, if a compound has an inhibitory activity against the enzyme so that it can be used to suppress gastric acid secretion and treat gastric ulcers.

JP 82-134417A and KR 91-7679A disclose some thiazole derivatives having anti-ulcer activity, and JP 81-5538A and U.S. Pat. No. 4,283,408 teach thiazole derivatives having an activity of suppressing the secretion of gastric juices.

However, there has been still a need to develop agents which are capable of reinforcing various defensive factors against the above described factors causing gastrointestinal ulcers.

The present inventors made extensive researches to provide novel compounds which can effectively inhibit $H^+/K^+$ ATPase. And a result thereof, they found out that the compounds represented by the general formula (I) given below showed not only a potent inhibitory activity against $H^+/K^+$ ATPase so that they can suppress the secretion of the gastric juices but also a significant cell protecting activity.

SUMMARY OF THE INVENTION

Therefore, an object of the present invention is to provide new thiazole derivatives represented by the following general formula (I):

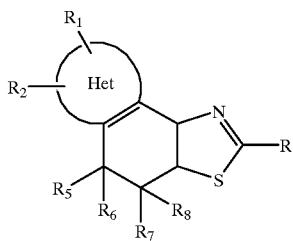

(I)

wherein,

R is hydrogen atom, a hydroxy group, a straight or branched $C_1-C_6$ lower alkyl group, a $C_1-C_4$ lower alkoxy group, phenyl group, a phenyl group having one to three substituents selected from a group consisting of a $C_1-C_4$ lower alkyl group, a $C_1-C_4$ lower alkoxy group, fluorine, chlorine, bromine and an amino group, a $C_1-C_5$ alkylphenyl group, a phenyl group having one to three substituents selected from a group consisting of a $C_1-C_4$ lower alkyl group, a $C_1-C_4$ lower alkoxy group, fluorine, chlorine, bromine and an amino group, a substituted or unsubstituted guanidino group, or an amino group having a general formula: $NR_3R_4$ in which $R_3$ and $R_4$ identical to or different from each other, represent independently a hydrogen atom, a $C_1-C_6$ lower alkyl group, a $C_3-C_6$ cycloalkyl group, a substituted or unsubstituted pyridyl group, a phenyl group having one to three substituents selected from a group consisting of a $C_1-C_4$ lower alkyl group, a $C_1-C_4$ lower alkoxy group, a halogen atom, an amino group, a cyano group and a nitro group, a piperidine group or $C_1-C_4$ alkylpiperidine group;

$R_1$ and $R_2$, identical to or different from each other, are independently a hydrogen atom, a hydroxy group, a $C_1-C_6$ lower alkyl group, phenyl group, a phenyl group having one substituent selected from a group consisting of a $C_1-C_4$ lower alkyl group, a $C_1-C_4$ lower alkoxy group, a halogen atom, a nitro and a cyano group, a $C_1-C_5$ alkylphenyl group, or a pyridine group;

$R_5$, $R_6$, $R_7$ and $R_8$, identical to or different from each other, are independently a hydrogen atom, a hydroxy group, a $C_1-C_4$ lower alkyl group, a $C_1-C_4$ lower alkoxy group, phenyl group, or a phenyl group substituted with a $C_1-C_4$ alkyl group, a $C_1-C_4$ alkoxy group or a halogen atom, or a $C_1-C_3$ alkylphenyl group;

Het is a 3-, 4- or 5-membered unsaturated monocyclic group, or 6- to 12-membered unsaturated fused cyclic group, said monocyclic and fused cyclic group being comprises of one or more hetero atoms selected from oxygen, oxidative nitrogen and oxidative sulfur atom, or their pharmaceutically acceptable salts.

According to the present invention, a method for producing the compounds is also provided.

The above and other objects and features of the present invention will be apparent to the skilled in the art from the following detailed description.

DETAILED DESCRIPTION OF THE INVENTION

Among the compounds (I) according to the present invention, the compounds (I) wherein R is hydrogen atom, or methyl, ethyl, isopropyl, methoxymethyl, ethoxymethyl, methoxyethyl, aryl, phenyl, benzyl, pyridine, or guanidinyl group, or an amino group having a general formula: $NR_3R_4$ in which $R_3$ and $R_4$, identical to or different from each other, represent independently a hydrogen atom, or methyl, ethyl, butyl, isopropyl, aryl, cyclopropyl, cyclobutyl, cyclohexyl, phenyl. benzyl, pyridine, piperidine, or 4-methyl piperidine group; $R_1$ and $R_2$ identical to or different from each other, are independently a hydrogen atom, a hydroxy group, or methyl, ethyl, isopropyl, methoxymethyl, ethoxymethyl, methoxyethyl, aryl, phenyl, benzyl, pyridine or guanidine group; $R_5$, $R_6$, $R_7$ and $R_8$, identical to or different from each other, are independently a hydrogen atom, a hydroxy group, or methyl, ethyl, isopropyl, methoxymethyl, ethoxymethyl, methoxyethyl, aryl, phenyl, or benzyl group, or fluorine, chlorine or bromine atom; and Het is a heterocyclic group such as thiazole, imidazothiazole, benzimidazothiazole, imidazopyridine or triazolothiazole group.

The pharmaceutically acceptable salts of the compound (I) of the present invention include acid-addition salts of the compound (I) with pharmaceutically acceptable organic and inorganic acids such as hydrochloric, hydrobromic, hydroiodic, phosphorous, sulfuric, nitrous, citric, formic, fumaric, maleic, tartaric, or malonic acids, an alkylsulfonic acid such as methanesulfonic acid, or an arylsulfonic acid such as p-toluene sulfonic acid.

The compound represented by the general formula (I) may be prepared from the compound represented by the general formula (II) by the reactions shown in the following reaction scheme I.

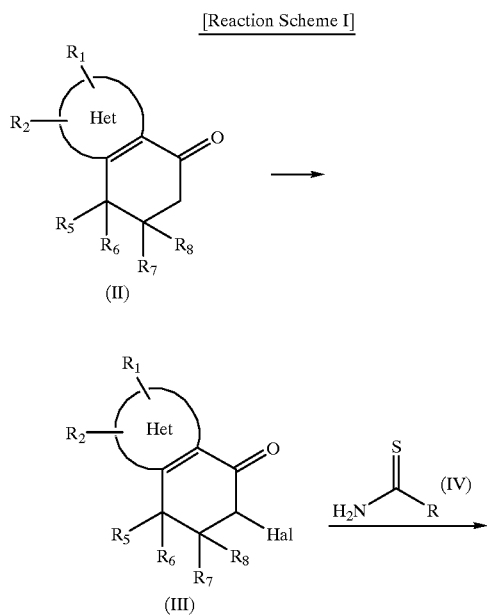

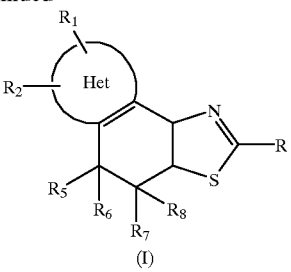

Wherein, R, $R_1$, $R_2$, $R_3$, $R_4$, $R_5$, $R_6$, $R_7$, and $R_8$ have the same meanings as defined above.

The reaction shown in Reaction Scheme I will be described in more detail hereinafter.

The compound (II) or its salt is dissolved into conc. aqueous solution of hydrobromic acid, and adding an equivalent halogen (particularly, bromine) while maintaining the solution at a temperature of 70° C. to 90° C. to give a compound (III) in the form of hydrogen halogenate. The hydrogen halogenate may be neutralized with a base in an aqueous system to give the compound (III).

The compound (III) or its salts is reacted with a substituted or unsubstituted thiourea, amidinothiourea, or thioamide in a solvent to give the thiazole derivative (I) of the present invention. The examples of the solvent, which may be employed for the reaction, may include, not limited thereto, acetone, ethanol, propanol, butanol, dimethylformamide, or dimethylsulfoxide and the like. The reaction may be carried out at a temperature or 50° C. to 100° C. The resulting compound (I) in the form of hydrogen halogenate can be further reacted with a base in an aqueous system to give the compound (I). The compound (I) may be further treated with various organic and inorganic acid to give its pharmaceutically acceptable acid addition salts. The examples of the inorganic or organic acids include those stated in the above.

The compound (II) employed for preparing the compound (I) may be prepared by the process shown in the following Reaction Scheme II.

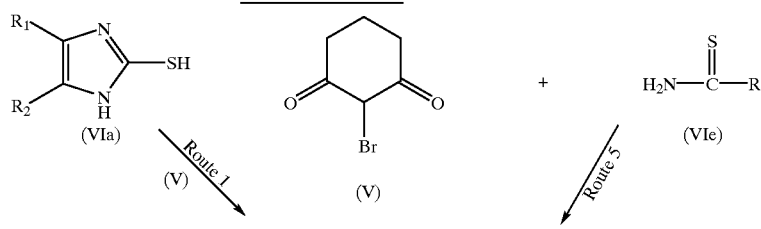

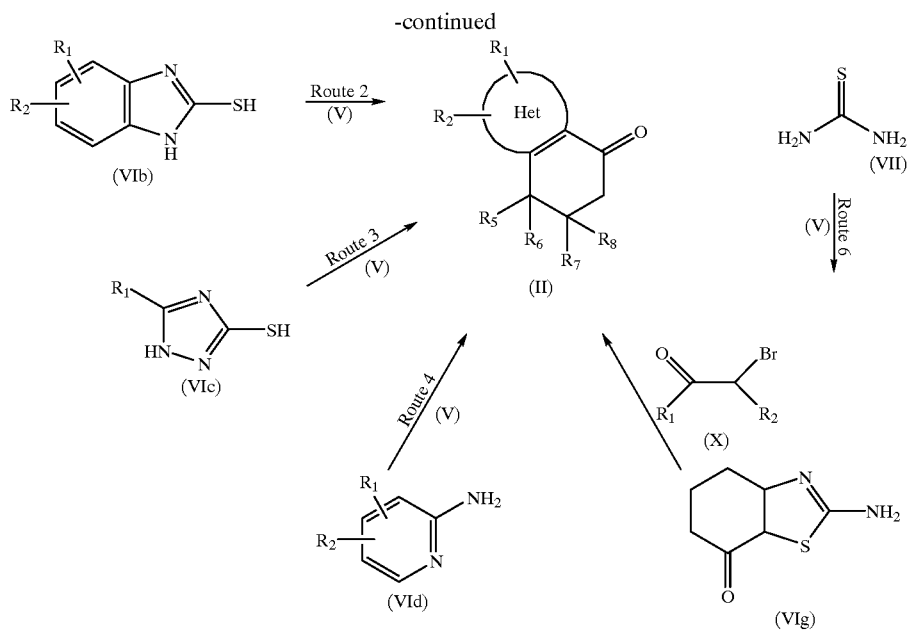

Wherein, R, $R_1$, $R_2$, $R_3$, $R_4$, $R_5$, $R_6$, $R_7$, $R_8$ and Het have the same meanings as defined above.

The compound (II) can be prepared by reacting a 2-bromo-1,3-cyclohexadione derivative (V) with 2-mercaptoimidazole (VIa) ("Route 1") 2-mercaptobenzimidazole (VIb) ("Route 2"), 3-mercaptotriazole (VIc) ("Route 3"), 2-aminopyridine (VId) ("Route 4") thioamide (VIe) ("Route 5") in a solvent. Alternatively, the compound (II) may be prepared by reacting the compound (X) with thiourea compound (VIg) which is prepared by reacting the compound (V) with thiourea compound (VIf). The example of the solvent may include, not limited thereto, ethanol, propanol, butanol, acetonitrile, 1,2-dimethoxyethane. The reaction is carried out at a temperature between 50° C. and the boiling point of the solvent employed. The resulting compound (II) in the form of hydrobromide is neutralized with a base in an aqueous system to give the compound (II).

The methods and results of pharmacological experiments and acute toxicity experiments carried out using the representative compounds (I) of the present invention are described below.

1. Inhibition of $H^+/K^+$ ATPase

Inhibition of $H^+/K^+$ ATPase, a proton carrying enzyme, was measured by following the procedure of Saccomani et al. [Biochim. Biophy. Acta., 465, 311–330 (1977)]. Thus, a homogenate of the gastric mucose membrane of rabbit was used to prepare vesicles containing $H^+/K^+$ ATPase by employing differential centrifugation and discontinuous density gradient centrifugation in Ficoll. The vesicles containing the enzyme were preincubated in a solution (0.5 ml) containing $1\times10^{-4}$M, $1\times10^{-5}$M, $1\times10^{-6}$M, or $1\times10^{-7}$M of the inventive compound (Example 21) and 5 mM of imidazole buffer (pH 7.4) at a temperature of about 37° C. for about 30 minutes. omeprazole was used as a control. A solution containing 2 mM of magnesium chloride, 40 mM of imidazole buffer (pH 7.4), 10 mM of potassium chloride and 10 mM of ATP was added to the mixture. The resulting mixture was incubated at 37° C. for 15 minutes and the reaction was terminated by adding 1 ml of ice-cold 22% solution of trichloroacetic acid. Enzyme activity was calculated by measuring the separated inorganic phosphate by following the method of Fiske and Subbarow [J. Biol. Chem., 66, 375–440 (1925)]. The concentrations ($IC_{50}$) of the test compounds which inhibit the enzyme activity by 50% are shown in Table 1.

TABLE 1

| Test compound | Enzyme Inhibition ($IC_{50}$) |
| --- | --- |
| Example 1 | $1.10 \times 10^{-6}$M |
| Example 2 | $2.16 \times 10^{-5}$M |
| Example 13 | $2.00 \times 10^{-4}$M |
| Example 14 | " |
| Example 15 | " |
| Example 16 | " |
| Example 17 | $4.90 \times 10^{-5}$M |
| Example 18 | $1.00 \times 10^{-4}$M |

2. Inhibition of Gastric Secretion

Inhibition of gastric secretion was measured by following the procedure of Shay ligation (Gastroenterology, 1954, 26, 903). Thus, male Sprague-Dawley rats weighing 180–200 g were starved for 24 hours and their pylorus were ligated. Then, the inventive compounds (Examples 1, 13 and 17) or omeprazole as a positive control was administered into duodenum. Four hours later, the stomach was removed, and the acidity and amount of gastric juice were measured. By comparing the measured values with the acidity and amount of the gastric juice of the stomach of the reference group to which no test compound was administered, the inhibition of gastric secretion was calculated. The effective dose ($ED_{50}$) of the test compounds which inhibit the gastric secretion by 50% are shown in Table 2.

TABLE 2

| Test Compound | Gastric juice Secretion Inhibition ($ED_{50}$, mg/kg) |
| --- | --- |
| Example 1 | 5.08 |
| Example 13 | 34.0% (25 mg/kg) |
| Example 17 | 15.4 |

3. Ulcer Inhibition
1) Inhibition of Ethanol-Induced Lesions

Inhibition activity of the inventive compound on the ethanol-induced ulcer was measured by using male sprague-Dawley rats weighing 180–200 g. Thus, rats were starved for 24 hours, and the inventive compound (Examples 1 and 17) or omeprazole as a positive control was orally administered. Thirty minutes later, absolute ethanol (5 ml/kg was orally administered. 1.5 hours later, the stomach was removed, and the degree of the wound of the stomach was measured. By comparing the measured values with the degree of the lesion of the stomach the reference group to which no test compound was administered, the effective dose ($ED_{50}$) of the test compounds which inhibit the lesion by 50% were calculated and are shown in Table 3.

2) Inhibition of Mepirizole-Induced Ulcer

Inhibition activity of the inventive compounds on the mepirizole-induced ulcers was measured by using male Sprague-Dawley rats weighing 200–230 g. Thus, rats were not starved, and the inventive compounds (Examples 1 and 17) or omeprazole as a positive control was orally administered. Thirty minutes later, mepirizole suspended in 1% CMC (250 mg/kg) was orally administered. Before administration, the rats were starved, the duodena were removed. The degree of the ulcer thereof was measured. By comparing the measured values with the degree of the ulcer of the duodena of the reference group to which no test compound was administered, the effective deses ($ED_{50}$) of the test compounds which inhibit the ulcer by 50% were calculated and are shown in Table 3.

3) Inhibition of Indomethacin-Induced Lesions

Inhibition activities of the inventive compounds on the indome]thacin-induced lesions was measured by using male Sprague-Dawley rats. Thus, rats were starved for 48 hours and prohibited from being supplied with water for 2 hours, and 35 mg/kg of indomethacin (Sigma Co.) as a causative of gastric lesions was subcutaneously administered. Before Indomethacine treatment, the inventive compounds (Examples 1 and 17) or omeprazole as a positive control was orally administered, and the inhibitions of lesions by the action of the test compounds were observed. The effective doses ($ED_{50}$) of the test compounds which inhibit the lesions by 50% were measured and are shown in Table 3.

4) Inhibition of Stress-Induced Ulcer

Inhibition activity of the inventive compound on the stress-induced ulcer was evaluated by using male Sprague-Dawley rats. Thus, rats were starved for 24 hours prior to carrying out the experiment.

Stress is an important factor for causing gastric lesions, and was applied to rats by immersing them in water.

Thirty minutes prior to immersing rats into water, the inventive compounds (Examples 1 and 17) or omeprazole as a positive control was orally administered, and the inhibitions of ulcer by the action of the test compounds were observed. The effective doses ($ED_{50}$) of the test compounds which inhibit the lesions by 50% were measured and are shown in Table 3.

5) Inhibition of Acetic Acid-Induced Ulcer

Inhibition activity of the inventive compound on-the acetic acid-induced ulcer was evaluated by using male Sprague-Dawley rats. Thus, rats were starved for 5 hours prior to carrying out the experiment.

20 Microliter of 30% acetic acid was injected into the submucosal layer of the stomach using a microsyringe to induce a circular ulcer on the stomach. Various doses of the inventive compounds (Examples 1 and 17) or omeprazole as a positive control were orally administered for 10 days, and the healing of ulcer by the action of the test compounds were observed. The percentages of the healing of the ulcer were calculated by comparing them with that of reference group.

TABLE 3

| Test Compound | Anti-ulcer activity ($ED_{50}$, mg/kg) | | | | |
|---|---|---|---|---|---|
| | Ethanol | Mepirizole | Indomethacin | Stress | Acetic acid* |
| Control (Omeprazole) | 17.1 | 2.8 | 1.2 | 4.4 | 27.1 |
| Inventive | | | | | |
| Ex. 1 | 30.8 | 2.6 | 2.95 | 9.2 | 22.67 |
| Ex. 17 | 2.91 | 18.67 | 4.68 | 17.56 | 31.59 |

*Percentage of healing in 30 mg/kg

4. Acute Toxicity

ICR mice (male and female) were orally administered with high dose (maximum dose: 5 g/kg) of inventive compound (Example 1) and were observed for their sudden death or a lasting of morbid conditions for 14 days. A median lethal dose ($LD_{50}$), an index of acute toxicity was measured and is shown in Table 4.

TABLE 4

| Compound | Sexuality | Dose (mg/kg) | No. of animals | No. of Death | Lethality (%) | $LD_{50}$ (mg/kg) |
|---|---|---|---|---|---|---|
| Ex. 1 | Male | 0 | 6 | 0 | 0 | >5000 |
| | | 40 | 6 | 0 | 0 | |
| | | 200 | 6 | 0 | 0 | |
| | | 1000 | 6 | 0 | 0 | |
| | | 5000 | 6 | 0 | 0 | |
| | Female | 0 | 6 | 0 | 0 | >5000 |
| | | 40 | 6 | 0 | 0 | |
| | | 200 | 6 | 0 | 0 | |
| | | 1000 | 6 | 0 | 0 | |
| | | 5000 | 6 | 0 | 0 | |

The present invention will be described in more detail by way of Examples.

EXAMPLE 1

Preparation of 2-amino-2,4-dihydro-8-phenylimidazo[2,1-b] benzothiazole

[Route 1]

(A) 2-Bromo-1,3-cyclohexadione 1,3-Cyclohexadione (19.6 g) was dissolved into distilled water (200 ml) at room temperature, and bromine (10.3 ml) was added dropwise at a temperature of below 5° C. The resulting precipitates were filtered, washed with cold water and dried to give the titled compound (34.9 g).

(B) 2-Phenyl-5,6-dihydroimidazo[2,1-b]benzothiazole-8 (7H)-one (Compound (IIa) in Reaction Scheme II)

2-Mercapto-4-phenylimidazole (10.6 g) and 2-bromo-1,3-cyclohexadione (12.6 g) were placed into absolute ethanol (200 ml) and the reaction mixture was heated to reflux for 16 hours and then cooled to give hydrobromide salt of the desired compound (16.3 g). The hydrobromide salt was neutralized with 10% sodium carbonate solution in an aqueous system to give the titled compound (12.3 g, 76%).

m.p.: 202–203° C. (240–241° C. for hydrobromide)

$^1$H-NMR (DMSO-$d_6$): δ2.23(m, 2H), 2.62(t, 2H), 3.10(t, 2H), 7.25–7.50(m, 3H), 7.89(d, 2H), 8.49(s, 1H)

(C) 7-Bromo-2-phenyl-5,6-dihydroimidazo[2,1-b] benzothiazole-8(7H)-one hydrobromide 2-Phenyl-5,6-dihydroimidazo[2,1-b]benzothiazole-8 (7H)-one hydrobromide (11.2 g) was placed into conc. hydrobromic acid (130 ml), and bromine (18.2 ml) was added dropwise to the reaction mixture while maintaining the temperature of 70–80° C. The reaction mixture was stirred at the same temperature for 2 hours, cooled, and washed with cold water to give yellow titled compound (12.8 g, 93%).

m.p. 214–216° C.

$^1$H-NMR (DMSO-d$_6$): δ2.60 (m, 1H), 2.80(m, 1H), 3.15–3.75(m, 2H), 5.13(m, 1H), 7.45(m, 3H), 7.98(m, 2H), 8.59(s, 1H)

(D) 2-Amino-2,4- dihydro-8-phenylimidazo[2,1-b]benzothiazole

7-Bromo-2-phenyl-5,6-dihydroimidazo[2,1-b]benzothiazole-8(7H)-one hydrobromide (6.22 g) and thiourea (1.22 g) were placed into absolute ethanol (90 ml), and the reaction mixture was heated to reflux for 3 hours and then cooled to give dihydrobromide of the desired compound (5.85 g). The dihydrobromide was neutralized with 10% potassium hydroxide solution in an aqueous system to give pale yellow solids, which were recrystallized with dimethylformamide (20 ml) to give the titled compound (3.1 g, 66%).

m.p.: 275–276° C. (248–250° C. for dihydrobromide)

$^1$H-NMR (CDCl$_3$): δ2.95–3.28(m, 4H), 7.15(br.s, 2H), 7.18–7.46(m, 3H), 7.87(d, 2H), 8.34(s, 1H)

[Route 2]

(A) 2-Amino-4,5-dihydrobenzothiazole-7(6H)-one

2-Bromo-1,3-cyclohexadione (30 g) prepared in Route 1 (A) was suspended into absolute ethanol, and thiourea (13) was added thereto. The reaction mixture was heated to reflux for 12–15 hours. After completion of the reaction, the reaction mixture was cooled to room temperature and concentrated under reduced pressure to evaporate the solvent. Acetone (70 ml) was added to the residue to give solids, which were filtered, washed with acetone (30 ml) and dried to give hydrobromide of the titled compound (27 g, 71%). The hydrobromide was neutralized with sodium hydroxide solution to give the titled compound (18 g, 68%)

(B) 2-Phenyl-5,6-dihydroimidazo[2,1-b]benzothiazole-8(7H)-one

2-Amino-4,5-dihydrobenzothiazole-7(6H)-one (18 g) prepared in the above (A) was dissolved into dimethylformamide (250 ml), and 2-bromoacetophenone (21,83 g) was added thereto followed by heating to reflux for 12–15 hours. After completion of the reaction, the reaction mixture was cooled to room temperature and placed into distilled water. The resulting precipitates were filtered, neutralized with sodium hydroxide solution, filtered, washed with ethyl acetate (100 ml), and dried to give the titled compound (21.25 g, 76%).

EXAMPLES 2–12

By following the procedure described in Example 1 by employing 7-bromo-2-phenyl-5,6-dihydroimidazo[2,1-b]benzothiazole-8(7H)-one hydrobromide (6.22 g) prepared in Example 1, Route 1 (D) and various thiourea derivatives for various reaction times, there were obtained inventive compounds of Examples 2–12. These compounds and their physical properties are shown in Table 5.

TABLE 5

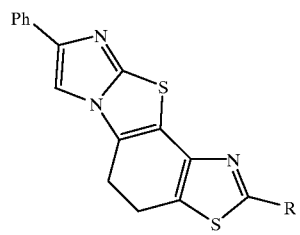

| Compd. | R | Yield (%) | mp (° C.) [HBr (° C.)] | $^1$H-NMR (DMSO-d$_6$): δ |
|---|---|---|---|---|
| Ex. 2 | Methylamino | 63<br>69 | 265–267<br>224–227 | 2.85(d, 3H), 3.12(m, 4H), 7.28(d, 1H), 7.40(dd, 2H), 7.64(bs.d, 1H), 7.88(d, 2H), 7.32(s, 1H) |
| Ex. 3 | Ethylamino | 63<br>69 | 251–254<br>254–257 | 1.20(t, 3H), 3.15(m, 4H), 3.27(qx5, 2H), 7.29(dd, 1H), 7.42(dd, 2H), 7.72(t, 1H), 7.88(d, 2H), 8.35(s, 1H) |
| Ex. 4 | Cyclopropylamino | 64<br>69 | 275–278<br>253–256 | 0.64(m, 2H), 0.78(m, 2H), 2.63(m, 1H), 3.18(m, 4H), 7.28(dd, 1H), 7.42(dd, 2H), 7.87(d, 2H), 8.14(s, 1H), 8.35(s, 1H) |
| Ex. 5 | 2-Methoxyethylamino | 54<br>57 | 220–222<br>213–216 | 3.13(m, 4H), 3.31(s, 3H), 3.42(m, 2H), 3.51(m, 2H), 7.29(dd, 1H), 7.42(dd, 2H), 7.81(bs, 1H), 7.88(d, 2H), 8.35(s, 1H) |
| Ex. 6 | Phenylamino | 55<br>59 | >300<br>>300 | 3.27(m, 4H), 7.12(dd, 1H), 7.38(dd, 1H), 7.47(m, 3H), 7.88(m, 4H), 8.05(d, 1H), 8.88(s, 1H) |
| Ex. 7 | Benzylamino | 66<br>68 | 258–260<br>235–237 | 3.15(m, 4H), 4.48(d, 2H), 7.21–7.48(m, 7H), 7.29(dd, 1H), 7.42(dd, 2H), 7.81(bs, 1H), 7.88(d, 2H), 8.35(s, 1H) |
| Ex. 8 | Allylamino | 59<br>61 | 234–237<br>230–234 | 3.17(m, 4H), 3.91(m, 2H), 5.21(m, 2H), 5.93(m, 1H), 7.28(dd, 1H), 7.41(dd, 2H), 7.38(d, 2H), 7.80(bs, 1H), 8.35(s, 1H) |
| Ex. 9 | Dimethylamino | 61<br>67 | 212–216<br>220–223 | 3.08(s, 6H), 3.19(m, 4H), 7.28(dd, 1H), 7.42(dd, 2H), 7.87(d, 2H), 8.32(s, 1H) |
| Ex. 10 | —N=C(NH$_2$)$_2$ | 42<br>45 | >300<br>>300 | 3.18(m, 4H), 6.88(bs, 4H), 7.28(dd, 1H), 7.42(dd, 2H), 7.88(d, 2H), 8.34(s, 1H) |
| Ex. 11 | 1-Piperazino | 65<br>81 | 284–288<br>290–294 | 3.08–3.28(m, 8H), 3.49–3.66(m, 4H), 7.29(dd, 1H), 7.43(dd, 1H), 7.88(d, 2H), 8.38(s, 1H) |
| Ex. 12 | 3-Pyridinyl | 50<br>51 | 245–248<br>248–252 | 3.38(m, 4H), 7.31(dd, 1H), 7.42(dd, 2H), 7.58(dd, 1H), 7.89(d, 2H), 8.10(d, 1H), 8.42(s, 1H), 8.70(d, 1H), 9.15(s, 1H) |

EXAMPLE 13

Preparation of 2-amino-4,5-dihydrobenzimidazo[2,1-b]thiazolo[5,4-g]benzothiazole dihydrobromide 2-Bromo-1,3-cyclohexadione prepared in Example 1, Route 1 (A) was reacted with 2-mercaptobenzimidazole in the same manner as that of Example 1, Route 1 (B) to give 1,2-dihydrobenzimidazo[2,1-b]benzothiazole-4(3H)-one (Compound (IIb) of Reaction Scheme II), which was subjected to bromination in the same manner as that of Example 1, Route 1 (C) to give 3-bromo-1,2-dihydrobenzimidazo[2,1-b]benzothiazole-4(3H)-one hydrobromide. The hydrobromide (1.45 g) and thiourea (0.15 g) were placed into ethanol (50 ml), and the mixture was heated to reflux for 2 hours, cooled, and the filtered to give the titled compound (61%).

m.p. above 300° C.

$^1$H-NMR (DMSO-$d_6$): $\delta$3.15(t, 2H), 3.55(t, 2H), 7.15 (br.s, 1H), 7.30(m, 2H), 7.70(d, 1H), 7.98(d, 1H)

EXAMPLES 14

Preparation of 2-amidino-4,5-dihydrobenzimidazo[2,1-b] thiazolo[5,4-g]benzothiazole 3-Bromo-1,2-dihydrobenzimidazo[2,1-b]benzothiazole-4 (3H)-one hydrobromide (1.0 g) prepared in Example 2 was reacted with amidinothiourea (0.59 g) in n-butanol (40 ml) while heating to reflux for 15 hours. After completion of the reaction, the reaction mixture was cooled and filtered to give dihydrobromide (0.65 g) of the desired compound. The dihydrobromide was neutralized with sodium carbonate solution in an aqueous system to give the titled compound (55%).

m.p. above 300° C. (above 300° C. for dihydrobromide)

$^1$H-NMR (DMSO-$d_6$): $\delta$3.30(t, 2H), 3.60(t, 2H), 6.90(s, 4H), 7.35(m, 2H), 7.70(d, 2H), 7.97(d, 1H)

EXAMPLE 15

Preparation of 2-amino-4,5-dihydro[1,2,4]triazolo[5,1-b] thiazolo[5,4-g]benzothiazole (A) 7-Bromo-5,6-dihydro[1,2,4]triazolo[5,1-b]benzothiazole-8 (7H)-one hydrobromide 2-Bromo-1,3-cyclohexadione (4.4 g) prepared in Example 1, Route 1 (A) and 1H-1,2,4-triazole-3-thiol (2.32 g) were dissolved into absolute ethanol (50 ml), and the reaction mixture was heated to reflux for 5 hours. After completion of the reaction, the reaction mixture was cooled and filtered to give 5,6-dihydro[1,2,4]triazolo[5,1-b]benzothiazole-8(7H)-one hydrobromide (2.84 g, compound (IIc) of Reaction Scheme II). The hydrobromide was dissolved into anhydrous acetic acid (20 ml) and an equivalent amount of bromine was added dropwise thereto at a temperature of 100° C., and the mixture was stirred at the same temperature for 30 minutes. The reaction mixture was cooled to give the titled compound (95%) as solids.

$^1$H-NMR (DMSO-$d_6$): $\delta$2.6(m, 2H), 2.8–2.91(m, 1H), 3.2–3.4(m, 2H), 5.15(t, 1H), 8.5(s, 1H)

(B)2-Amino-4,5-dihydro[1,2,4]triazolo[5,1-b]thiazolo[5,4-g]benzothiazole

7-Bromo-5,6-dihydro[1,2,4]triazolo[5,1-b]benzothiazole-8(7H)-one hydrobromide (1.3 g) prepared in the above (A) and thiourea (1.06 g) were dissolved into ethanol (50 ml), and the solution was heated to reflux for 2 hours. After completion of the reaction, the reaction mixture was cooled and filtered to give solids (0.6 g), which are dihydrobromide of the desired compound. The dihydrobromide was neutralized with sodium carbonate in an aqueous system to give the titled compound (60%).

m.p. above 300° C.

$^1$H-NMR (DMSO-$d_6$):$\delta$3.1(t, 2H), 3.28(t, 2H), 7.25(br.s, NH$_2$), 8.31(s, 1H)

EXAMPLES 16

Preparation of 2-amidino-4,5-dihydro [1,2,4]triazolo [5,1-b] thiazolo[5,4-g]benzothiazole 7-Bromo-5,6-dihydro[1,2-]triazolo[3,2-b]benzothiazole-8(7H)-one hydrobromide (1.3 g) prepared in Example 4 (A) was reacted with amidinothiourea (1.41 g) in ethanol (50 ml) while heating to reflux for 4.5 hours. After completion of the reaction, the reaction mixture was cooled and filtered to give dihydrobromide (0.82 g) of the desired compound. The dihydrobromide was neutralized with sodium carbonate solution in an aqueous system to give the titled compound (73%).

m.p. above 300° C.

$^1$H-NMR (DMSO-$d_6$): $\delta$3.1(t, 2H), 3.25(t, 2H), 6.85(br.s, 2NH$_2$), 8.3(s, 1H)

EXAMPLE 17

Preparation of 2-amino-4,5-dihydropyrido[1,2-a] thiazolo [5,4-g]benzimidazole (A) 6,7-Dihydropyrido[1,2-a]benzimidazole-9(8H)-one (Compound (IId) of Reaction Scheme II)

2-Bromo-1,3-cyclohexadione (9.55 g) prepared in Example 1, Route 1 (A) and 2-aminopyridine (4.7 g) were dissolved into absolute ethanol (200 ml), and the reaction mixture was heated to reflux for 20 hours. After completion of the reaction, the reaction mixture was concentrated under reduced pressure, and the residue was dissolved into water. The solution was neutralized with sodium carbonate, extracted with chloroform three times, dried over magnesium sulfate, and concentrated under reduced pressure. The residue was purified by silica gel column chromatography (eluant:methylene chloride: acetonitrile=2:1) to give the titled compound (3.0 g, 32%).

$^1$H-NMR (DMSO-$d_6$): $\delta$2.18(m, 2H), 2.6(m, 2H), 2.98(t, 2H), 7.25 (t, 1H), 7.72 (m, 2H), 9.2 (d, 1H)

(B) 2-amino-4,5-dihydropyrido[1,2-a]thiazolo[5,4-g] benzimidazole 6,7-Dihydropyrido[1,2-a]benzimidazole-9 (8H)-one prepared in the above (A) was subjected to bromination in the similar manner to that of Example 1, Route 1(C) to give 8-bromo-6,7-dihydropyrido[1,2-a]benzimidazole-9(8H)-one hydrobromide. The resulting compound (17.4 g) and thiourea (6.0 g) were dissolved into absolute ethanol (200 ml), and the solution was heated to reflux for 4 hours. After completion of the reaction, the reaction mixture was cooled and filtered to give solids (10.6 g), which are dihydrobromide of the desired compound. The dihydrobromide was neutralized with 2N-potassium hydroxide in an aqueous system and recrystallized with a mixture of DMF and ethanol to give the titled compound (7.1 g, 56%).

m.p. 249° C.

$^1$H-NMR (DMSO-$d_6$) $\delta$3.1(m, 4H), 7.28(s, NH$_2$), 7.50(t, 1H), 7.75(t, 1H), 7.92(d, 1H), 9.10(d, 1H)

EXAMPLE 18

Preparation of 2-amidino-7-amino-4,5-dihydrobenzo [1,2-d:3,4-d']bisthiazole (A) 2-Amidino-6-bromo-4,5-dihydrobenzothiazole-7(6H)-one 2-Bromo-1,3-cyclohexadione prepared in Example 1, Route 1 (A) was reacted with amidinothiourea in the similar manner to that of Example 1, Route 1(B) to give 2-amidino-4,5-dihydrobenzothiazole-7(6H)-one hydrobromide. The hydrobromide (3.4 g) was dissolved into conc. hydrobromic acid (20 ml), and one equivalent of bromine was added dropwise at a temperature of 85° C. The mixture was stirred at a temperature of 80° C. to 90° C. for 30 minutes, cooled and filtered. The solids were neutralized with sodium carbonate to give the titled compound (3.17 g, 67%).

$^1$H-NMR (DMSO-d$_6$): δ2.0–2.45(m, 2H), 2.5–2.85(m, 2H), 4.8(t, 2H), 7.3(br.s, 2NH$_2$)

(B)2-amidino-7-amino-4,5-dihydrobenzo[1,2-d:3,4-d'] bisthiazole

2-Amidino-6-bromo-4,5-dihydrobenzothiazole-7(6H)-one (1.4 g) prepared in the above (A) was reacted with thiourea (0.38 g) in ethanol while heating to reflux for 3 hours. After completion of the reaction, the reaction mixture was cooled and filtered to give hydrobromide of the desired compound (0.5 g). The hydrobromide was neutralized with sodium carbonate in an aqueous system to give the titled compound (22%).

m.p. above 300° C. (above 300° C. for hydrobromide)

$^1$H-NMR (DMSO-d$_6$): δ2.85(m, 4H), 6.9(br.s, NH$_2$), 7.6 (br.s, 2NH$_2$)

It is understood that the foregoing detailed description is given merely by way of illustration and that modifications and variations may be made therein without departing from the spirit and scope of the invention.

We claim:

1. A compound represented by the following general formula (I):

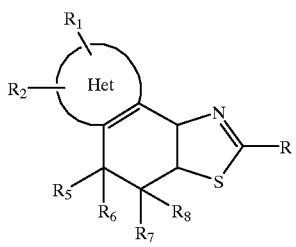

(I)

wherein,

R is a hydrogen atom, or a methyl, ethyl, isopropyl, aryl, phenyl, benzyl, or guanidinyl group, or an amino group having the general formula: NR$_3$R$_4$ in which R$_3$ and R$_4$, identical to or different from each other, represent independently a hydrogen atom, or a methyl, ethyl, butyl, isopropyl, aryl, cyclopropyl, cyclohexyl, phenyl, benzyl, pyridine, piperidine, or 4-methyl piperidine group; p1 R$^1$ and R$_2$, identical to or different from each other, are independently a hydrogen atom, a hydroxy group, a C$_1$–C$_6$ lower alkyl group, a phenyl group, a phenyl group having one substituent selected from a group consisting of a C$_1$–C$_4$ lower alkyl group, a C$_1$–C$_4$ lower alkoxy group, a halogen atom, a nitro and a cyano group, a C$_1$–C$_5$ alkylphenyl group, or a pyridine group;

R$_1$ R$_6$, R$_7$ and R$_8$, identical to or different from each other, are independently a hydrogen atom, a hydroxy group, a C$_1$–C$_4$ lower alkyl group, a C$_1$–C$_4$ lower alkoxy group, phenyl group, or a phenyl group substituted with a C$_1$–C$_4$ alkyl group, a C$_1$–C$_4$ alkoxy group or a halogen atom, or a C$_1$–C$_3$ alkylphenyl group with the proviso that R$_7$ is not H nor CH$_3$ when Het is a 5-membered unsaturated oxygen-containing monocyclic group; and Het is selected from the group consisting of thiazole, imidazothiazole, benzimidazothiazole, imidazopyridine and triazolothiazole group, or a pharmaceutically acceptable salt thereof.

2. The compound (I) according to claim 1, which is 2-amino-4,5-dihydro-8-phenylimidazo [2,1-b]thiazolo[5,4-g]benzothiazole, or a pharmaceutically acceptable salt thereof.

3. The compound (I) according to claim 1, which is 2-amino-4,5-dihydropyrido[1,2-a]thiazolo[5,4-g] benzimidazole, or a pharmaceutically acceptable salt thereof.

* * * * *

UNITED STATES PATENT AND TRADEMARK OFFICE
CERTIFICATE OF CORRECTION

PATENT NO. : 6,043,373
DATED : March 28, 2000
INVENTOR(S) : Yoo et al.

Page 1 of 2

It is certified that error appears in the above-indentified patent and that said Letters Patent is hereby corrected as shown below:

In the claims, column 14, line 4, cancel beginning with "R is a hydrogen atom," to and including "$R_1$, $R_6$, $R_7$ and $R_8$," in column 14, line 19, and insert the following:

--R is a hydrogen atom, or a methyl, ethyl, isopropyl, aryl, phenyl, benzyl, or guanidinyl group, or an amino group having the general formula: $NR_3R_4$ in which $R_3$ and $R_4$, identical to or different from each other, represent independently a hydrogen atom, or a methyl, ethyl, butyl, isopropyl, aryl, cyclopropyl, cyclohexyl, phenyl, benzyl, pyridine, piperidine, or 4-methyl piperidine group;

$R_1$ and $R_2$, identical to or different from each other, are independently a hydrogen atom, a hydroxy group, a $C_1$-$C_6$ lower alkyl group, a phenyl group, a phenyl group having one substituent selected from a group consisting of a $C_1$-$C_4$ lower alkyl group, a $C_1$-$C_4$ lower alkoxy group, a halogen atom, a nitro and a cyano group, a $C_1$-$C_5$

UNITED STATES PATENT AND TRADEMARK OFFICE
CERTIFICATE OF CORRECTION

PATENT NO. : 6,043,373
DATED : March 28, 2000
INVENTOR(S) : Yoo et al.

It is certified that error appears in the above-indentified patent and that said Letters Patent is hereby corrected as shown below:

alkylphenyl group, or a pyridine group;

$R_5$, $R_6$, $R_7$ and $R_8$,--.

Signed and Sealed this

Twenty-seventh Day of March, 2001

Attest:

Attesting Officer

NICHOLAS P. GODICI

Acting Director of the United States Patent and Trademark Office

UNITED STATES PATENT AND TRADEMARK OFFICE
CERTIFICATE OF CORRECTION

PATENT NO. : 6,043,373  Page 1 of 3
DATED : March 28, 2000
INVENTOR(S) : Yoo et al.

It is certified that error appears in the above-identified patent and that said Letters Patent is hereby corrected as shown below:

Title page,
Item [57], ABSTRACT,

Replace general formula (I) with --

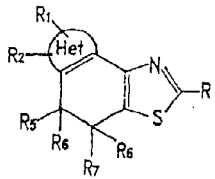

--

Column 1,
Lines 47 – 59, replace general formula (I) with --

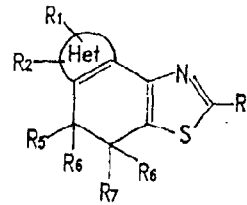

--

Column 4,
Lines 3 – 12, replace general formula (I) with --

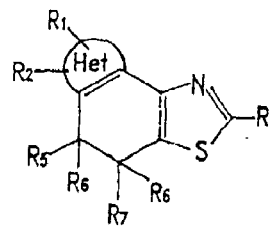

--

UNITED STATES PATENT AND TRADEMARK OFFICE
CERTIFICATE OF CORRECTION

PATENT NO.    : 6,043,373
DATED         : March 28, 2000
INVENTOR(S)   : Yoo et al.

It is certified that error appears in the above-identified patent and that said Letters Patent is hereby corrected as shown below:

<u>Column 14,</u>
Line 4, cancel beginning with "R is a hydrogen atom," to and including "$R_1$, $R_6$, $R_7$ and $R_8$,"

Line 19, and insert the following:
-- R is a hydrogen atom, or a methyl, ethyl, isopropyl, aryl, phenyl, benzyl, or guanidinyl group, or an amino group having the general formula: $NR_3R_4$ in which $R_3$ and $R_4$, identical to or different from each other, represent independently a hydrogen atom, or a methyl, ethyl, butyl, isopropyl, aryl, cyclopropyl, cyclohexyl, phenyl, benzyl, pyridine, piperidine, or 4-methyl piperidine group;
$R_1$ and $R_2$, identical to or different from each other, are independently a hydrogen atom, a hydroxy group, a $C_1$-$C_6$ lower alkyl group, a phenyl group, a phenyl group having one substituent selected from a group consisting of a $C_1$-$C_4$ lower alkyl group, a C1-$C_4$ lower alkoxy group, a halogen atom, a nitro and a cyano group, a $C_1$-$C_5$ alkylphenyl group, or a pyridine group;
$R_5$, $R_6$, $R_7$ and $R_8$, --.

<u>Columns 5 and 6,</u>
Replace Reaction Scheme II, general Formula (VIg) with

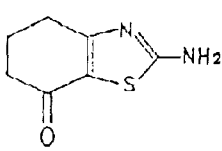

UNITED STATES PATENT AND TRADEMARK OFFICE
CERTIFICATE OF CORRECTION

PATENT NO.    : 6,043,373
DATED         : March 28, 2000
INVENTOR(S)   : Yoo et al.

It is certified that error appears in the above-identified patent and that said Letters Patent is hereby corrected as shown below:

<u>Column 13,</u>
Lines 33 – 43, replace general formula (I) with

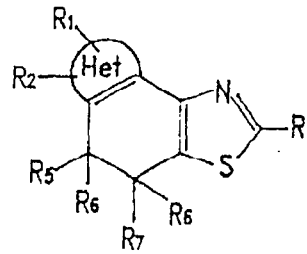

Signed and Sealed this

Tenth Day of December, 2002

JAMES E. ROGAN
*Director of the United States Patent and Trademark Office*